United States Patent
Garoff et al.

(10) Patent No.: US 6,875,721 B1
(45) Date of Patent: Apr. 5, 2005

(54) SOLUBLE MAGNESIUM DIHALIDE COMPLEX, PREPARATION AND USE

(75) Inventors: Thomas Garoff, Helsinki (FI); Timo Leinonen, Tolkkinen (FI); Sirpa Ala-Huikku, Helsinki (FI)

(73) Assignee: Borealis Technology Oy, Porvoo (FI)

(*) Notice: Subject to any disclaimer, the term of this patent is extended or adjusted under 35 U.S.C. 154(b) by 0 days.

(21) Appl. No.: 09/582,321

(22) PCT Filed: Dec. 21, 1998

(86) PCT No.: PCT/FI98/01004

§ 371 (c)(1),
(2), (4) Date: Aug. 25, 2000

(87) PCT Pub. No.: WO99/33843

PCT Pub. Date: Jul. 8, 1999

(30) Foreign Application Priority Data

Dec. 23, 1997 (FI) .................................. 974622
Dec. 23, 1997 (FI) .................................. 974623

(51) Int. Cl.⁷ .............................................. B01J 31/00
(52) U.S. Cl. .............................................. 502/172
(58) Field of Search ................................... 502/172

(56) References Cited

U.S. PATENT DOCUMENTS

| | | | |
|---|---|---|---|
| 4,727,051 A | | 2/1988 | Breen et al. |
| 5,100,849 A | * | 3/1992 | Miya et al. .................... 502/9 |
| 5,188,999 A | * | 2/1993 | Duranel et al. ............. 502/111 |
| 5,710,229 A | * | 1/1998 | Garoff et al. ................ 526/348 |
| 5,767,215 A | * | 6/1998 | Garoff et al. ................ 526/348 |
| 6,200,923 B1 | * | 3/2001 | Garoff et al. ................ 502/127 |
| 6,235,854 B1 | * | 5/2001 | Kioka et al. ................. 526/119 |
| 6,420,499 B1 | * | 7/2002 | Garoff et al. ............. 526/123.1 |

FOREIGN PATENT DOCUMENTS

| | | |
|---|---|---|
| EP | A2297076 | 12/1988 |
| EP | A3683175 | 11/1995 |
| FI | 92837 | 9/1994 |
| FI | 99247 | 9/1997 |

\* cited by examiner

*Primary Examiner*—Mark L. Bell
*Assistant Examiner*—Jennine Brown
(74) *Attorney, Agent, or Firm*—Birch, Stewart, Kolasch & Birch, LLP

(57) ABSTRACT

The invention relates to a complex comprising a magnesium dihalide and an electron donor. It is a complex of the magnesium dihalide and the electron donor and has the formula (I):

$$MgX_2 \cdot [R(OR')_n]_m \quad (I)$$

Figure 1:
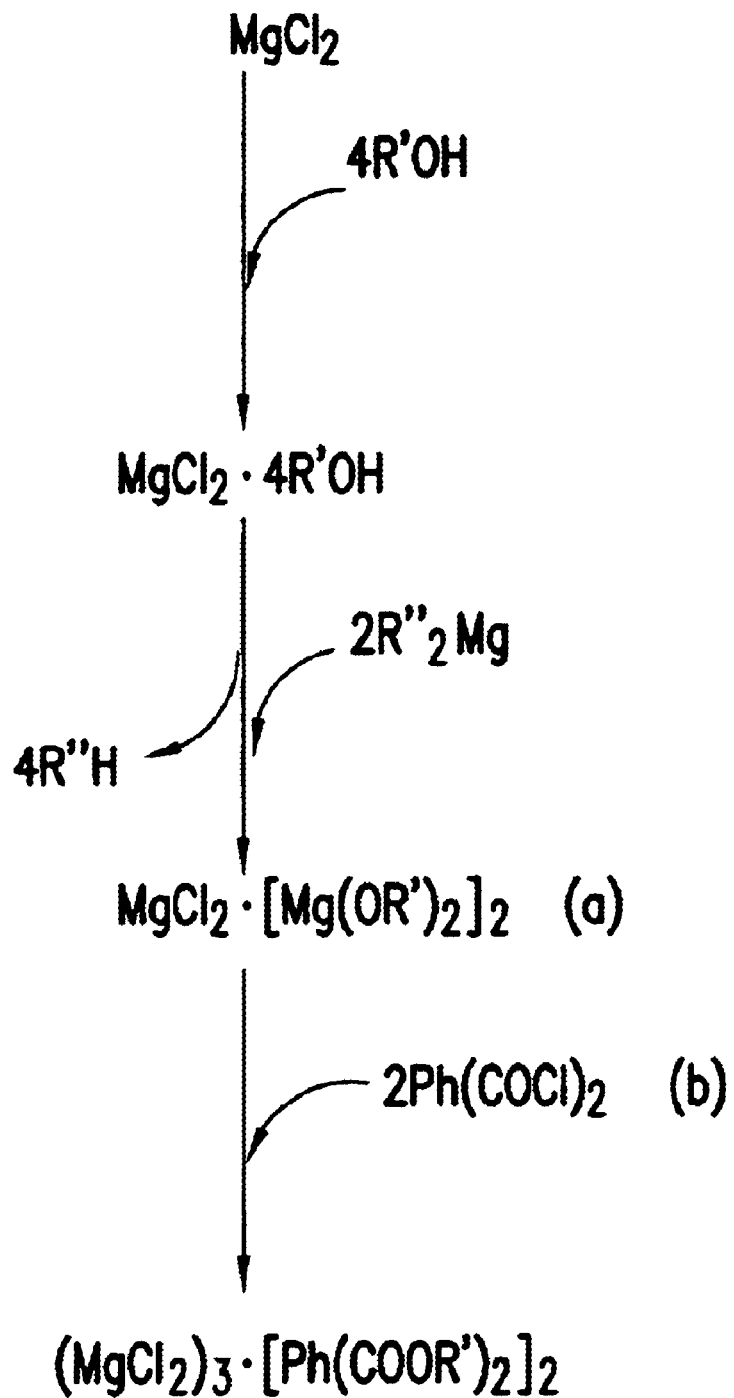

wherein $MgX_2$ is the magnesium dihalide and $R(OR')_n$ is the electron donor, X is a halogen, R is an n-valent $C_1$–$C_{20}$ aliphatic group, an n-valent $C_7$–$C_{27}$ araliphatic group or an n-valent $C_2$–$C_{22}$ acylic group, R' is a $C_1$–$C_{20}$ alkyl group or a $C_7$–$C_{27}$ aralkyl group, n is a number from 1 to 6 and m is defined as a number $0.5 \leq m \leq 2.0$. The invention also relates to the preparation process of such a complex, as well as the use thereof for the preparation of olefin polymerization catalyst components.

28 Claims, 5 Drawing Sheets

THE X-RAY DIFFRACTION PATTERN OF THE Mg–COMPLEX PRODUCED OUT OF Mg–ALKYL, ALCOHOL AND PHTHALIC ESTER (EXAMPLE 2)

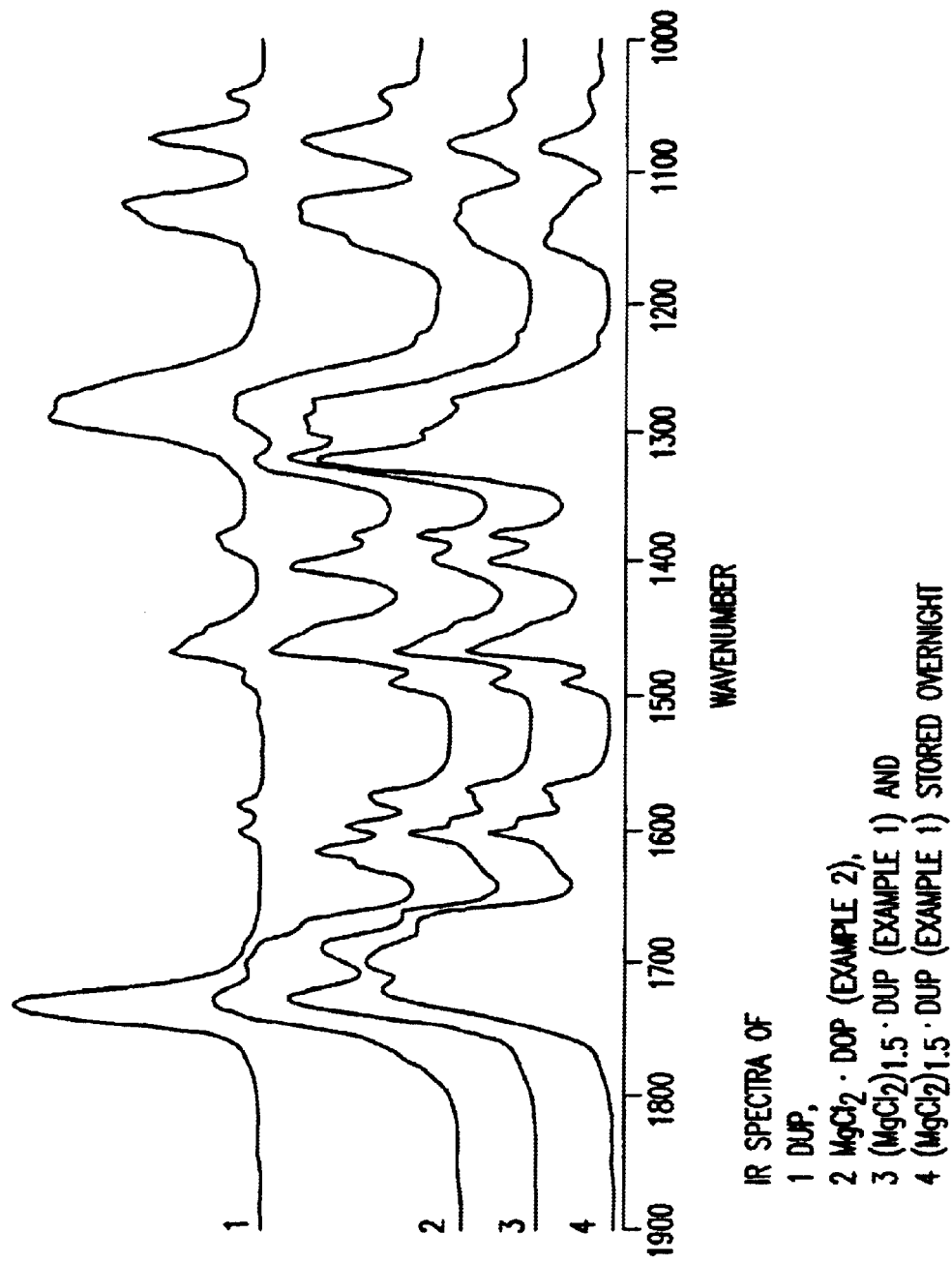

SOLUBLE MAGNESIUM DIHALIDE COMPLEX, PREPARATION AND USE

This application is the national phase under 35 U.S.C. § 371 of PCT International Application No. PCT/FI98/01004 which has an International filing date of Dec. 21, 1998, which designated the United States of America.

The invention relates to a soluble complex comprising a magnesium dihalide and an electron donor. The invention also relates to a process for the preparation of such a complex, as well as the use of such a complex for the preparation of a polymerization catalyst component containing magnesium, transition metal, halogen and electron donor.

A complex is, according to Römpps Chemie-Lexikon, 7. Edition, Franckh'sche Verlagshandlung, W. Keller Co., Stuttgart, 1973, page 1831, "a derived name of compounds of higher order, which originates from the combination of molecules,—unlike compounds of first order, in the creation of which atoms participate".

Generally, so called Ziegler-Natta catalyst components have been prepared by reacting a magnesium dihalide-alcohol complex compound or a magnesium alkoxide non-complex compound with a titanium halide and an electron donor which usually is a phthalic acid ester. It is necessary that the magnesium dihalide is amorphous for the catalyst component to be active. Amorphous magnesium dihalide is thus produced in situ.

When reacting the titanium halide with the magnesium dihalide-alcohol complex compound or the magnesium alkoxide non-complex compound, the titanium halide form titanium alkoxy trihalide, which is a harmful waste product. Both reactions have the disadvantage that the titanium halide is wasted for other purposes than the direct provision of catalytically active sites, such as chlorination of the magnesium reactant and washing away of the harmful titanium alkoxy trihalide.

In the production of amorphous magnesium dihalide, such as $MgCl_2$ strong polar ligand groups ($L_1$) are needed in order to break up the strong electrostatic crystallinic bonds between the $MgCl_2$ molecules according to reaction (1):

$$xMgCl_2 + xL_1 = x(Cl_2Mg - L_1) \quad (1)$$

In practice, polar solvents are needed to carry out reaction (1). In several cases these polar solvents are reactive towards other parts of the catalyst component, and thus have to be replaced by less polar solvents ($L_2$). These less polar solvents are, however, often unable to react and co-ordinate with $MgCl_2$ due to the strong intermolecular forces in the $MgCl_2$ structure (2):

$$xMgCl_2 + xL_2 = \text{No reaction} \quad (2)$$

Typical examples of solvents that are able to form complexes with $MgCl_2$ are alcohols and water. These compounds have, however, a reactive hydrogen in the hydroxyl group of their molecule which easily reacts with other compounds such as titaniumhalides. Examples of less reactive solvents are the organic esters. They are less reactive towards other components but at the same time they do not have the ability to break up the strongly co-ordinated $MgCl_2$ molecules. In view of the teaching of the prior art, it seems impossible to achieve amorphous $MgCl_2$ without harmful side reactions.

EP-A-0 297 076 discloses adducts of magnesium dihalides with alcohols as electron donors for the use as starting materials for the preparation of olefin polymerization catalysts. Alcohols have a reactive hydrogen which react with titanium halides.

The purpose of the invention is therefore to produce amorphous magnesium dihalide in situ without wasting titanium halide or producing harmful waste products. The invention also aims at a stoichiometric route for the preparation of Ziegler-Natta catalyst components and their intermediates. By a stoichiometric route, new catalyst components for the production of tailor-made olefin polymers can be produced.

The purposes of the invention has been achieved by means of a complex comprising a magnesium dihalide and an electron donor, which is characterized in that it is a complex of the magnesium dihalide and the electron donor and has the formula (I):

$$MgX_2 \cdot [R(OR')_n]_m \quad (I)$$

wherein $MgX_2$ is the magnesium dihalide and $R(OR')_n$ is the electron donor, X is a halogen, R is an n-valent $C_1$–$C_{20}$ aliphatic group, an n-valent $C_7$–$C_{27}$ araliphatic group or an n-valent $C_2$–$C_{22}$ acylic group, R' is a $C_1$–$C_{20}$ alkyl group or a $C_7$–$C_{27}$ alkyl group, n is a number from 1 to 6 and m is defined as a number $0.5 \leq m \leq 2.0$. By "n-valent acylic group" is meant a group having n acyl moieties.

Formula (I) is an empirical or semiempirical formula, i.e. m expresses the ratio between the the electron donor $R(OR')_n$ and magnesium dihalide $MgX_2$. The structural formula may have several molecules of $MgX_2$ and several same or different molecules of $R(OR')_n$, such as in the complex $(MgX_2')_a \cdot [R(OR')_n]_b$ wherein b:a=m. See e.g. formula (III) below. The claimed complex may be a statistical one, being a mixture of complexes having the average formula (I), or a specific one, essentially all the molecules of which having the same formula (I).

In the magnesium dihalide molecular component $MgX_2$ of the complex, X is preferably selected from Cl, Br and I, and is most preferably Cl. The most preferred complex according to the invention is thus a magnesiun dichloride complex.

In the electron donor molecular component $R(OR')_n$ of the complex, R is preferably an n-valent $C_2$–$C_{22}$ acylic group, more preferably an n-valent aromatic $C_7$–$C_{22}$ acylic group, most preferably phthaloyl. R' is preferably a $C_6$–$C_{16}$ all, most preferably a $C_6$–$C_{12}$ alkyl like undecyl or 2-ethyl-1-hexyl. It means that the phthalate preferably should be an ester of phthalic acid and a longer-chained alcohol. n is preferably about 1 to about 4, preferably about 2, meaning preference for a phthalic acid diester (phthalic acid is dibasic). By "acylic group" is meant the general name for organic acid groups, which form the remainder of carboxylic acids after removing the hydroxyl group.

Thus, the most preferred complex is that of one of the most efficient magnesium compounds and one of the most efficient internal electron donors in the art of Ziegler-Natta catalysts, namely magnesium dichloride and a phthalic acid ester.

In the claimed complex as a whole, m depicts the average ratio between the electron donor molecular component $R(OR')_n$ and the magnesium dihalide molecular component $MgX_2$. m is preferably about 0.67 to about 1.0, most preferably about, 0.67 or about 1.0. See below, structural formulas (II) and (III).

The complex according to the invention is preferably a magnesium dichloride phthalic acid ester complex having the formula $MgCl_2 \cdot [C_6H_4(COOR')_2]_m$, wherein R' is the same as above and m is from 0.5 to 2.0, most preferably from 0.6 to 1.8.

According to one embodiment of the complex of the invention, the complex is preferably a magnesium dichloride phthalic acid ester complex having the structural formula (II):

$$MgCl_2 \cdot C_6H_4(COOR')_2 \qquad (I)$$

wherein R' is the same as above.

According to another embodiment of the complex of the invention, the complex is a magnesium dichloride phthalic acid ester complex having the structural formula $$(MgCl_2)_3 \cdot [C_6H_4(COOR')_2]_2 \qquad (III)$$

wherein R' is the same as above.

Typically, the claimed complex has an X-ray diffraction pattern (measured by a Siemens D500 instrument equipped with a Cu anode and a graphite monochromator in the reflected beam and using an effect of 40 kV and 35 mA and a CuKα radiation wavelength of 1.541 Å), showing a dominant peak at 4.°2Θ.

The invention also relates to a process for the preparation of a complex comprising a magnesium dihalide and an electron donor.

Characteristic of the claimed process is that a magnesium compound (a) containing an alkoxy moiety, which magnesium compound is selected from the group consisting of a complex of a magnesium dihalide and a magnesium dialkoxide, a complex of a magnesium dihalide and an alcohol, and a non-complex magnesium dialkoxide, is reacted with a halogen compound (b), which is capable of forming the electron donor by replacement of its halogen by said alkoxy moiety.

According to the most important aspect of the invention, the process is a part of a novel stoichiometric preparation process leading to novel catalyst components for olefin polymerization.

The halogen compound (b) is capable of forming the electron donor by replacement of its halogen by said alkoxy moiety. This does not only mean that the halogen compound is a reagent leading to the electron donor, but also that it is a structural precursor thereof. Compare e.g. an alkyl halide with the corresponding dialkyl ether or an organic acid halide with the corresponding organic acid ester.

The halogen compound (b) preferably has the formula (IV):

$$RX_n \qquad (IV)$$

wherein R is an n-valent $C_1$–$C_{20}$ aliphatic group, an n-valent $C_7$–$C_{27}$ araliphatic group or an n-valent $C_2$–$C_{22}$ acylic group, X is a halogen and n is 1 to 6. In the formula, R is preferably an n-valent $C_2$–$C_{22}$ acylic group, more preferably an n-valent aromatic $C_7$–$C_{22}$ acylic group, most preferably phthaloyl. X is preferably selected from Cl, Br and L and is preferably Cl. n is preferably 1 to 4, most preferably about 2.

According to a preferred embodiment of the process of the invention, said halogen compound (b) is an organic acid halide, preferably phthalic acid dichloride $Ph(COCl)_2$, wherein Ph is o-phenylene. When one considers that the most preferred internal electron donor molecule of the claimed complex is a phthalic acid ester, the complexed ester molecule is simply formed by replacing the chlorines of the phthalic acid dichloride with alkoxy groups.

According to a first alternative embodiment of the process of the invention, said magnesium compound (a) containing an alkoxy moiety is a magnesium dichloride-magnesium dialkoxide complex of the formula (V):

$$MgCl_2 \cdot [Mg(OR')_2]_p \qquad (V)$$

wherein R' is a $C_1$–$C_{20}$ alkyl group or a $C_7$–$C_{27}$ aralkyl group, preferably a $C_6$–$C_{16}$ alkyl group, and p is 1 to 6, preferably about 2. Formula (V) is empirical or semiempirical, meaning that the complex's molecular clusters can consist of several $MgCl_2$ molecules and several $Mg(OR')_2$ molecules, corresponding to the formula $(MgCl_2)c[Mg(OR')_2]d$ wherein d:c=p. In the process of the invention, said magnesium dichloride-magnesium dialkoxide complex is reacted with the above halogen compound so that the halogen compound (b) has its halogen(s) replaced by the alkoxide(s) of the complex and forms an electron donor, whereby the complex of magnesium dichloride and the electron donor is formed.

Preferably, said complex of a magnesium dihalide and a magnesium dialkoxide is a magnesium dichloride-dimagnesium dialkoxide complex of the structural formula (VI):

$$MgCl_2 \cdot [Mg(OR')_2]_2 \qquad (VI)$$

wherein R' is a $C_1$–$C_{20}$ alkyl group or a $C_7$–$C_{27}$ aralkyl group, preferably a $C_6$–$C_{16}$ alkyl group.

Said magnesium dichloride-magnesium dialkoxide complex is preferably prepared by reacting magnesium dichloride and an alcohol into an intermediate which is a magnesium dichloride-alcohol complex $MgCl_2 \cdot (R'OH)_{2p}$ wherein R' is the same as above, and reacting the magnesium dichloride alcohol complex with p mol of a magnesium dialkyl $MgR''_2$, wherein R'' is a hydrocarbyl group having 1 to 20 carbon atoms. If R'' is a hydrocarbyl group having 1 to 5 carbon atoms, a volatile alkane R''H byproduct is thereby formed and easily removed by evaporation. In the synthesis, the molar ratio $MgCl_2$:R'OH is preferably between 1:1 and 1:8, most preferably between 1:2 and 1:5. The molar ratio $MgCl_2$ $(R'OH)_{2p}$:$MgR''_2$ is preferably between 1:1 and 1:4, most preferably about 1:2.

Said magnesium compound (a) which is said magnesium dichloride-dimagnesium dialkoxide complex $MgCl_2 \cdot [Mg(OR')_2]_2$, wherein R' is the same as above, is preferably reacted with said halogen compound (b) which is said phthalic acid dichloride $Ph(COCl)_2$, wherein Ph is o-phenylene. Typically, the product is $(MgCl_2)_3 \cdot [Ph(COOR')]_2$. See formula (III) above.

In the first alternative embodiment of the claimed process, said magnesium compound (a) and said halogen compound (b) are reacted in essentially stoichio-metrical amounts and, independently, at a temperature of between 80° C. and 160° C. The reaction time is preferably about 2 h to about 8 h.

Most preferably, the magnesium dihalide and the alcohol which is a heavier alcohol, are first reacted at a temperature between 120° C. and 160° C., after which the product is reacted with the magnesium alkoxide at a temperature between 80° C. and 120° C., followed by reaction with the halogen compound at said lower temperature interval.

A typical example of said first alternative embodiment of the claimed process is described in FIG. 1.

According to a second alternative embodiment of the claimed process, said magnesium compound (a) containing an alkoxy moiety is a non-complex magnesium dialkoxide of the formula (VII):

$$Mg(OR')_2 \qquad (VII)$$

wherein R' is a $C_1$–$C_{20}$ aralkyl group or a $C_7$–$C_{27}$ aralkyl group, preferably a $C_6$–$C_{16}$ alkyl group.

Said non-complex magnesium dialkoxide is preferably prepared by reacting a magnesium dialkyl, preferably a magnesium dialkyl of the formula MgR"$_2$, wherein R" is a hydrocarbyl group having 1 to 20 carbon atoms, and an alcohol, preferably an alcohol of the formula R'OH, wherein R' is the same as above. The preferred ratio between the magnesium dialkyl and the alcohol is about 1:2.

In the second alternative embodiment of the claimed process, said magnesium compound (a) which is said non-complex magnesium dialkoxide, has the formula Mg(OR')$_2$, wherein R' is a C$_1$–C$_{20}$ aralkyl or a C$_7$–C$_{27}$ aralkyl, preferably a C$_6$–C$_{16}$ alkyl, is preferably reacted with said halogen compound (b) which is said phthalic acid dichloride Ph(COCl)$_2$, wherein Ph is o-phenylene. Usually, said magnesium compound (a) and said halogen compound (b) are reacted in essentially stoichiometric amounts. The product formed is preferably MgCl$_2$.Ph(COOR')$_2$. See Formula II above.

Figure 2:
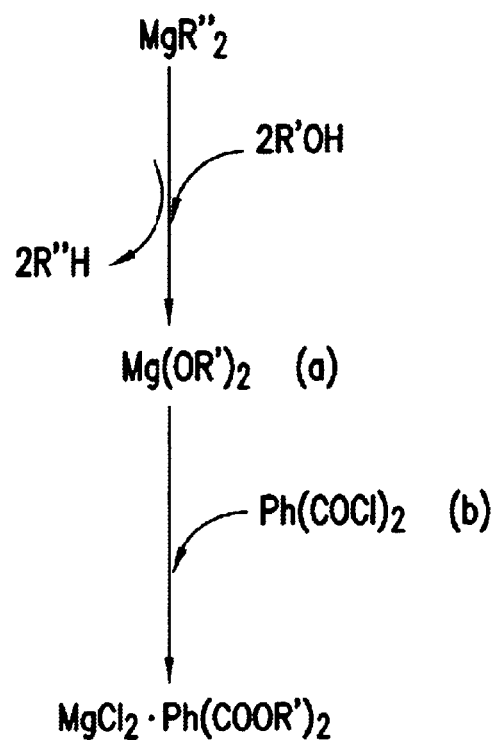

A typical example of said second alternative embodiment of the claimed process is described in FIG. 2.

According to a third alternative embodiment of the process of the invention, said magnesium compound (a) containing an alkoxy moiety is a complex of a magnesium dihalide and an alcohol of the Formula (VIII):

MgCl$_2$.(R'OH)$_q$     (VIII)

wherein R' is a C$_1$–C$_{20}$ alkyl group or a C$_7$–C$_{27}$ aralkyl group, preferably a C$_6$–C$_{16}$ alkyl group, and q is from 1 and 6. The alkoxy moiety is the R'O group of the alcohol R'OH. This complex is often used as starting material for Ziegler-Natta catalyst components. However, it is not known to have been used as starting material for a magnesium dihalide electron donor complex by reacting it with a halogenous electron donor precursor in the above described way.

The complex of a magnesium dihalide and an alcohol is usually prepared by reacting magnesium dichloride MgCl$_2$ and and alcohol R'OH, wherein R' is the same as above.

Figure 3:
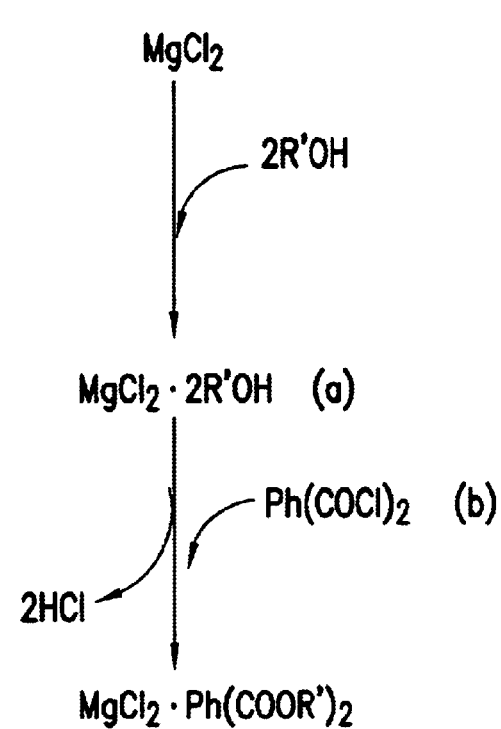

In the process according to the second alternative embodiment, said magnesium compound (a) which is said complex of a magnesium dihalide and an alcohol having the formula MgCl$_2$.(R'OH)$_q$, wherein R' is a C$_1$–C$_{20}$ alkyl or a C$_7$–C$_{27}$ aralkyl, preferably a C$_6$–C$_{16}$ alkyl, and q is from 1 and 6, is preferably reacted with said halogen compound (b) which is said phthalic acid dichloride Ph(COCl)$_2$, wherein Ph is o-phenylene. An example of this third alternative embodiment is described in FIG. 3.

Above, the product and its preparation according to the invention have been described. As the claimed complex finds its natural application in the field of olefin polymerization catalyst synthesis, the invention also relates to the use of said complex in that field. Thus, claimed is the use of said complex for the preparation of a polymerization catalyst component containing magnesium, as well as at least one transition metal, halogen and electron donor. More specifically, the use is characterized in that said complex is reacted with a titanium halide (c) to give said catalyst component.

Said titanium halide (c) preferably has the Formula (IX):

(OR''')$_p$TiX$_{4-p}$     (IX)

wherein R''' is a C$_1$–C$_{10}$ alkyl group or a C$_7$–C$_{16}$ aralkyl group, X is a halogen and p is 0 to 3. Most preferably, said titanium halide (c) is a titanium tetrahalide TiX$_4$, wherein X is the same as above, most preferably titanium tetrachloride TiC4.

Experimental

Preparation of the complexes

All chemicals were handled in strict inert conditions and all the reactions took place also in strict inert conditions in a nitrogen atmosphere.

EXAMPLE 1

First Alternative Embodiment

First 1.07 g (11.2 mmol) of MgCl$_2$ was introduced into a 50 ml glass reactor. 9.60 ml (8.0 g, 46.2 mmol) of 1-undecanol was added on to the MgCl$_2$. The slurry was mixed using a magnetic stirring bar and the solution was heated to 130° C. and the reactants were allowed to react with each other at this temperature for 3 h. The slurry was cooled down to 100° C. and 9.6 ml (8.3 g, 90 mmol) of toluene was added to the reaction solution to increase its dissolving capability. 25.40 ml (18.52 g, 22.3 mmol R"$_{12}$ Mg) of a 20% heptane solution of butyl-octyl magnesium was now introduced. Finally, 3.24 ml (4.565 g, 22.5 mmol) of phthaloyl chloride was added. The achieved product was dried under a stream of nitrogen for several hours at temperatures between 90° C. and 120° C.

EXAMPLE 2

Second Alternative Embodiment 123.2 mmol of butyl-octyl magnesium was introduced into a 250 ml glass reactor. A 20% heptane solution of the butyl-octyl magnesium containing 2.92 w-% of Mg was used giving a feed volume of 139.4 ml (102.5 g) in the reactor. 244.6 mmol (38.2 ml, 31.85 g) of 2-ethyl-1-hexanol was then added slowly at room temperature. The addition of alcohol took 23 min. Mixing speed was about 240 rpm. The temperature was increased to 63° C. and the reactants were allowed to react with each other at that temperature for 15 min. After this 122.74 mmol (17.69 ml, 24.92 g) of phthaloyl chloride was added slowly at room temperature. The temperature was increased during 10 min to 50° C. and the reactants were again allowed to react with each other at that temperature for 5 min. After this the reaction solution was allowed to cool down to room temperature.

28.8 g of the achieved solution was taken into a 100 ml glass reactor for solvent evaporation. The sample was dried under vacuum in a stream of nitrogen gas at 50° C. for 3 h. 12 ml of condensed solvent (heptane) was trapped in the vacuum trap.

The product was washed with 60 ml of pentane at 45° C. for 45 min, after which the product was allowed to settle for 45 min and the solid product was separated from the solution. The product was washed a second time with 44 ml of pentane and finally dried under vacuum and in a stream of nitrogen at 50° C. for one hour.

EXAMPLE 3

Third Alternative Embodiment 22.60 mmol (2.15 g) of MgCl$_2$ was introduced into a 100 ml glass reactor. To this, 45.19 mmol (7.10 ml, 5.92 g) of 2-ethyl-1-hexanol was added. Finally, 22.60 mmol. (3.26 ml, 4.59 g) of phthaloyl dichloride was added to the mixture. The mixture was kept under agitation at 60° C. for 30 min. A solid complex was collected from the vessel by evaporation and washed three times with a 100 ml portion of heptane at 90° C. for 15 min, then with a 100 ml portion of pentane at room temperature and finally dried. This product was reacted with TiCl$_4$ into a catalytically active complex.

COMPARATIVE EXAMPLE

A fourth sample was prepared by introducing 20 mmol MgCl$_2$ (1.90 g) in a 150 ml glass reactor equipped with a magnetic stirrer. 20 mmol of di-2-ethyl-hexyl-phthalate (8.0 ml, 7.81 g) (DOP) was then added on to the $MgCl_2$. The reactants were allowed to react with each other overnight. The product was washed with pentane and dried in the same way as described above.

Characterization of the products by X-ray diffractometry and Infrared spectroscopy The products were characterized by infrared spectroscopy (IR) and by taking X-ray diffraction patterns of it. The WAXS patterns were collected in reflection mode between 2 and 70°2 θ with a Siemens D500 instrument. The diffractometer was equipped with a Cu anode and a graphite monochromator in the reflected beam. The effect used was 40 kV and 35 mA. The CuKα radiation wavelength was 1.541 Å. The sample was loaded in a glove box into a Mylar film covered sample holder.

Di-undecylphthalate (DUP) was used as electron donor reference in the IR studies. The products of examples 1 and 2 were investigated together with the standard DUP. The products of example 1 was analyzed twice: right away and a second time after overnight storage.

The IR spectra were taken by a Nicolet 510 FTIR equipment with 2 $cm^{-1}$ resolution. The number of scans were 128. All the samples were investigated as capillary films between two KBr pellets. Pure DUP was not handled in inert conditions, but the $MgCl_2$ samples were handled in a glove box in an inert nitrogen environment in order to protect the samples from air and moisture. To get thin enough capillary films the samples were somewhat heated when placed in between the KBr pellets.

X-Ray Characterization

Figure 4:
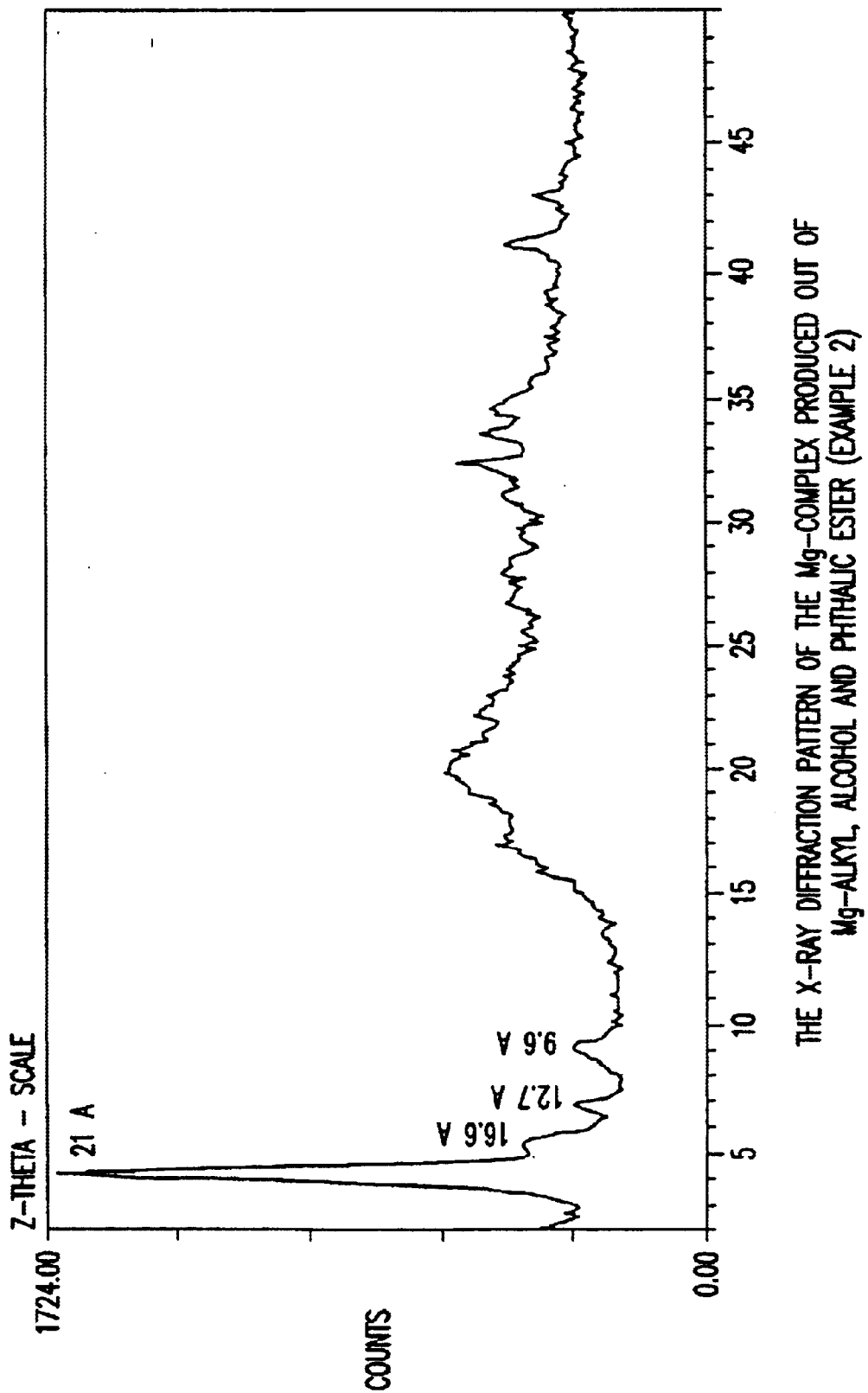

The X-ray diffraction pattern of the $MgCl_2$-DOP complex is shown in FIG. 4. The OD pattern show no sign of $MgCl_2$. At 50° 2Θ), where the most significant peak of pure $MgCl_2$ is to be found, there is no sign of a peak. This is also the case at 30° and 35° 2Θ. On the other hand, there is a new dominant peak at 4.5° 2Θ) showing that the reflecting layers have been separated far from each other (21 Å).

Figure 5:
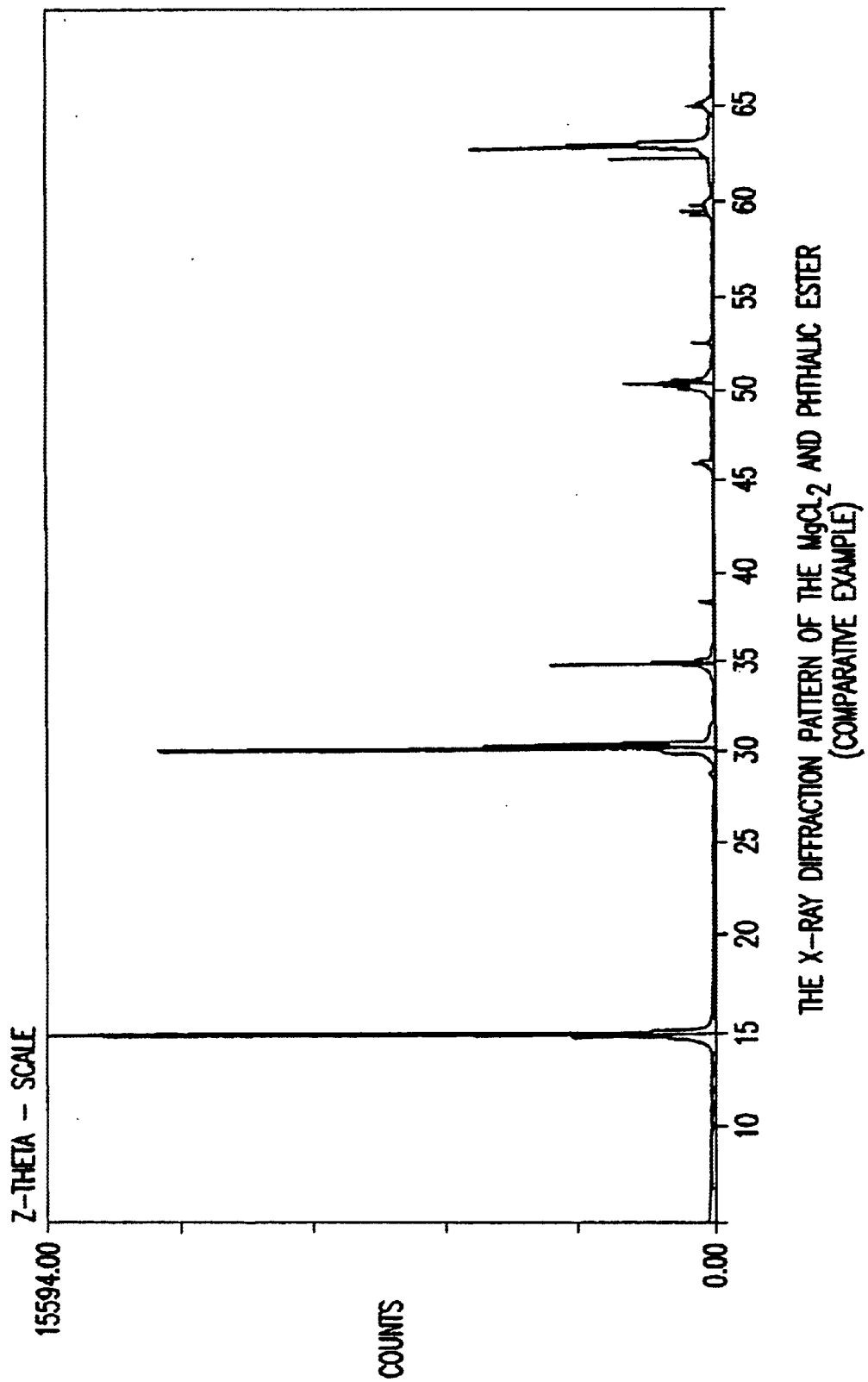

The X-ray diffraction pattern of the product coming from the direct reaction between $MgCl_2$ and DOP of the comparative example is shown in FIG. 5. The pattern showed that no reaction between these components had occurred, the X-ray pattern showed pure $MgCl_2$ with its significant reflecting signals at 15°, 30°, 35° and 50° 2Θ.

The results show that in the first three synthesis routes the donor compound had been complexed with $MgCl_2$ at a molecular level, thereby breaking up the strong molecular structure of crystaline $MgCl_2$ and indicating in situ preparation thereof. The results show also that in the fourth, direct synthesis route, the donor compound had not been able to form a complex with $MgCl_2$ but the product contained only original $MgCl_2$.

Results by Infrared Spectroscopy

The samples were prepared and studied by IR spectroscopy according to the description in the experimental section above. As $MgCl_2$ does not have any absorbance spectrum in the IR area from 4000 to 400 $cm^{-1}$, the IR study concentrated on the changes in the structure of the DOP and DUP complexation to the $MgCl_2$.

The pure DOP and DUP absorbs IR light due to the stretching vibration of the ester carbonyl double bond of the C=O group at the wavelength of 1729 $cm^{-1}$. The corresponding stretching vibration of the C—O— bond is to be found at 1280 $cm^{-1}$ and at 1100 $cm^{-1}$ (see FIG. 6).

When the $MgCl_2$ was co-ordinated to DOP in the molar ratio of 1:1, clear changes in the IR spectrum of DOP could be seen (FIG. 6, Example 2). The absorption peaks of pure DOP could still clearly be seen which indicates that a part of the carbonyl groups are still unco-ordinated. On the right side of the original C=O absorption peak there is a new shoulder indicating that a part of the C=O groups have co-ordinated to Mg causing the double bond of the C=O group to loosen up starting to resemble more a single C—O bond. The proportionally small shift in the position of the "shoulder peak" indicate a weak interaction, i.e. a weak co-ordination of $MgCl_2$ to the C=O oxygen. A weak interaction is also indicated by the sign of several secondary "shoulder" peaks.

When the $MgCl_2$ amount was increased by 50% in the complex (Example 1), the proportion of the "shoulder" peak at about 1690 $cm^{-1}$ increased. There is however no sign of a strong coordination (FIG. 6). The changes in the IR spectra show up even better in the sample that had been stored overnight. Here the main peak of the carbonyl oxygen has shifted from the position of 1729 $cm^{-1}$ for the pure DUP to 1719 $cm^{-1}$. The results show also that the coordinated carboxyl group is influencing the "free" carboxyl group as the position of its peak is shifted 10 $cm^{-1}$.

The same results can be seen in connection with the absorption peak of the C—O— bond. The absorption peak of the C—O— bond in the pure DUP is found at 1287 $cm^{-1}$. Looking at the spectra for the $MgCl_2$.DOP (Example 2) and the $(MgCl_2)_{1.5}$.DUP (Example 1) samples there is a corresponding "shoulder" peak forming to the left of the original peak indicating a weak double bond character of the C—O bond. This shift is so strong that the original peak at $1287^{-1}$ is not any longer detectable in the product that had been stored overnight (FIG. 6). These results indicate that the Mg in the $MgCl_2$ is complexed between the C=O oxygen and the C—O oxygen atoms in the $MgCl_2$.DOP and in the MgCl2.DUP complex.

Conclusively it can be said that in the IR spectrum of the pure DUP the peaks show uncoordinated carbonyl groups, in the $MgCl_2$.DOP and in the $MgCl_2$.DUP sample (Example 2) there is a $MgCl_2$ co-ordination to one of the carbonyl groups, the other being free, and in the $(MgCl_2)_{1.5}$.DUP sample (Example 1) there is a partial co-ordination of $MgCl_2$ to both of the carbonyl groups.

EXAMPLES 4 to 7

Use of the Complex According to the First Alternative Embodiment

Preparation of the Catalyst Component Complex 1.69 g (17.70 mmol) of anhydrous $MgCl_2$ was introduced in inert conditions into a 100 ml septum bottle. 11.12 ml (9.27 g, 70.80 mmol) of 2-ethyl-hexanol (EHA) was introduced on to the $MgCl_2$ and after this the temperature was increased to 125–128° C. to allow the reaction components to react with each other. After this, 8.81 ml (7.67 g, 83.19 mmol) of toluene was added after the reaction solution had cooled down to 110° C. After the addition of the toluene the reaction solution was cooled down to 21° C. Then 40 ml (29.16 g, 35.4 mmol) of a 20 w-% heptane solution of butyl-octyl-magnesium (BOMAG) was added. After this 5.10 ml (7.19 g, 35.4 mmol) of phthaloyl dichloride (PDC) was added to produce a $MgCl_2$ donor complex solution.

Use of the Catalyst Component Complex

The $MgCl_2$ donor complex according to the first alternative embodiment was now, drop by drop, added into 38.91 ml (67.16 g, 354 mmol) of $TiCl_4$ and allowed to react with this reagent at a temperature of 95° C. The reactants were allowed to react with each other for 30 min.

After the $TiCl_4$ treatment, the complex was allowed to settle and the liquid was siphoned off. After this, 100 ml (86.6 g, 0.94 mol) of toluene was added on to the complex and the complex was washed in this solution at 90° C. for 20 min. Depending on which of the synthesis was under work, this washing step was done once (Example 1), twice (Example 2), three times (Example 3) or four times (Example 4). Finally, the catalyst complex was washed twice with 65 ml (44.44 g, 0.44 mol) portions of heptane for 20 min at 80° C. and thereafter, the complex was washed at room temperature with a 55 ml (34.44 g, 0.48 mol) portion of pentane for 20 min to improve the drying conditions. The catalysts were dried under a stream of nitrogen for one hour.

Chemical Characterization of the Complexes

The catalyst complexes were characterized with respect to their chemical composition by measuring their Ti and Cl content. The Ti analysis was started by dissolving the samples in a mixture of nitric and hydrofluoric acid. The metal was measured flame atomic absorption with a nitrous acetylene flame. Chloride was determined after dissolution in dilute sulphuric acid by potentiometric titration with a standard silver nitrate solution.

Determination of Donors and Phthalic Anhydride

The determination of the phthalic esters and the phthalic anhydride were done by first dissolving the sample in acetone. The dissolving was improved by keeping the acetone slurry in an ultra-sound bath for 5 min. After this the samples were filtered and run by solution chromatography. As eluent a solution consisting of water and acetonitrile in the proportion of 4/96 was used. Eluent flow rate was 1.5 ml/min. A photo diode array was used as detector. Each component was identified by comparing the respective retention time and UV spectra with standard components.

GC Studies to Measure Alcohol Content

To check the conversion rate of the ethanol (EtOH), 2-ethyl-hexanol (EHA), or other alcohol added in the synthesis, the alcohol content of the catalysts were measured by gas chromatography (GC). This was done by first dissolving a 100 mg sample of the catalyst in 1 ml of n-pentanol. Depending on the alcohol to be measured, an internal alcohol standard was chosen. If ethanol was to be measured the n-pentanol solution contained n-propenol as internal standard. To improve the solubility of the catalyst in the solution, the sample was kept in an ultra-sound bath. To remove the inorganics from the organic solution it was extracted with 1 ml of water and to ensure full dissolution, another ml of the n-pentanol solution was added. To ensure repeatable equilibrium conditions between the organic layer and the water layer the samples were allowed to stand overnight. The sample for the GC was taken from the alcohol layer. A Hewlett Packard 5890 GC with a 60 m DB-1 column was used for the GC analyses. The column had a diameter of 0.25 mm with a film thickness of 1 μm. An FID detector was used.

Bulk Polymerization

Propylene was polymerized in stirred tank reactor having a volume of 5l. About 0.9 ml triethyl aluminium (TEA) as a cocatalyst, ca 0,12 ml of a 100-% solution of cyclohexyl methyl dimethoxy silane as an external donor and 30 ml of n-pentane were mixed and allowed to react for 5 minutes. Half of the mixture was added to the polymerization reactor and the other half was mixed with ca 20 mg of the catalyst complex. After additional 5 minutes the catalyst/TEA/donor/n-heptane mixture was introduced into the reactor. The Al/Ti mole ratio was 250 and the Al/external donor mol ratio was 10 mol/mol. 70 mmol hydrogen and 1400 g of propylene were introduced into the reactor and the temperature was raised within 15–30 minutes to 70° C. The polymerization time was 60 minutes, after which the polymer formed was taken out from the reactor. The polymers were characterized with respect to their Melt Flow Rate ($MFR_2$), bulk density (BD) and fraction of total solubles in xylene (TS).

Results

Preparation of the Complexes

The catalyst complexes achieved in this investigation are listed in Table 1.

TABLE 1

The catalyst complexes prepared

| Example | Number of toluene washes | Colour of catalyst | Morphology of catalyst |
|---|---|---|---|
| 4 | 1 | Dark wine-red | Freely flowing |
| 5 | 2 | Dark wine-red | Freely flowing |
| 6 | 3 | Dark wine-red | Freely flowing |
| 7 | 4 | Dark wine-red | Freely flowing |

The Chemical Composition of the Catalysts

The chemical composition of the catalysts were measured according to the description in the experimental section. In Table 2 the chemical composition of the catalysts are listed in w-% units, in Table 3 the composition is listed in mol-% units and in Table 4 the molar proportions between Mg, Ti and DOP are compared.

The chemical compositions of the catalysts were as expected on the basis of the reaction equation. With three washes a composition of $(MgCl_2)_6TiCl_4DOP$ was achieved. During the washes, there was a slightly higher wash out of $TiCl_4$ compared to DOP in the last catalyst. The amount of free alcohol (EHA) was also very low playing no significant part in the chemical composition (now 0.004–0.006 mol-%), i.e. being about 5% of the mol amount of $TiCl_4$ or DOP. The amount of phthalic anhydride was about 50% of the DOP amount. To sum up the results from the chemical measurements it can be said that the chemical composition of the catalyst complex when using the $MgCl_2$ enriched $Mg(OR')_2$ as a reagent in the catalyst synthesis is $(MgCl_2)_3TiCl_4DOP(PA)_{0.5}$

TABLE 2

The chemical composition of the catalysts in w-% units

| Example | Mg w-% | Ti w-% | DOP w-% | EHA w-% | PA w-% |
|---|---|---|---|---|---|
| 4 | 7.8 | 4.7 | 33.6 | 0.72 | 6.7 |
| 5 | 8.1 | 4.7 | 32.0 | 0.54 | 7.4 |
| 6 | 10.2 | 3.2 | 28.5 | 0.58 | 6.5 |
| 7 | 12.9 | 1.6 | 21.6 | 0.51 | 6.1 |

TABLE 3

The chemical composition of the catalysts in mol-% units

| Example | Mg mol-% | Ti mol-% | DOP mol-% | EHA mol-% | PA mol-% |
|---|---|---|---|---|---|
| 4 | 0.321 | 0.098 | 0.086 | 0.0055 | 0.045 |
| 5 | 0.333 | 0.098 | 0.082 | 0.0041 | 0.050 |
| 6 | 0.420 | 0.067 | 0.073 | 0.0045 | 0.044 |
| 7 | 0.531 | 0.033 | 0.056 | 0.0039 | 0.041 |

TABLE 4

The molar ratio between Mg, Ti and DOP

| Example | Mg | Ti | DOP |
|---|---|---|---|
| 4 | 3.3 | 1 | 0.9 |
| 5 | 3.4 | 1 | 0.8 |
| 6 | 6.3 | 1 | 1.1 |
| 7 | 15.9 | 1 | 1.7 |

Calculated and Found Chlorine Contents

The chlorine content in the catalysts were calculated on the basis of the Mg and Ti content. The calculations were based on the assumption the Mg was present in the catalyst as $MgCl_2$ and Ti as $TiCl_4$. These calculated results were then compared to the measured results. The results are listed in Table 5. The results showed to be in good agreement, which indicates that both Mg and Ti are present in the catalyst complexes in the fully chlorinated form.

TABLE 5

The calculated and the found chlorine content in the catalysts

| Example | Calculated Cl w-% | Found Cl w-% |
|---|---|---|
| 4 | 36.7 | 36.9 |
| 5 | 37.6 | 38.0 |
| 6 | 39.3 | 39.7 |
| 7 | 42.4 | 43.8 |

Wash out of $TiCl_4$.DOP

All the chemical measurements support the same conclusion: due to the toluene, $TiCl_4$ and DOP are washed out from the catalyst in a molar proportion of 1:1. This shows up as a constant decrease of the Ti mol-% and the DOP mol-%, and as a constant increase of the Mg mol-% and the Cl mol-%.

Activity of the Catalysts

All the catalyst complexes were test polymerized according to the descriptions in the experimental section. The results are listed in Table 5. The results showed that all the catalyst complexes had about the same activity, being between 1.0 and 1.5 kg PP/g cat.

TABLE 6

The test polymerization results

| Example | Activity kg PP/2 cat | Activity kg PP/g Ti |
|---|---|---|
| 4 | 1.1 | 23 |
| 5 | 1.2 | 26 |
| 6 | 1.5 | 45 |
| 7 | 1.3 | 81 |

MFR of the Polymers

In Table 7 the MFR values achieved from the test polymerization results are listed. The results indicated a systematic increase in MFR with increasing number of toluene washes as MFR increases from 2.0 in the first polymer to 13.7 in the third.

TABLE 7

The MFR values of the polymers

| Example | MFR |
|---|---|
| 4 | 2.0 |
| 5 | 4.9 |
| 6 | 13.7 |
| 7 | 12.4 |

EXAMPLES 8 to 13

Use of the Complex According to the Second Alternative Embodiment

Preparation of the Catalyst Component Complexes

All chemicals were handled in strict inert conditions and all the reactions took place also in strict inert conditions in nitrogen atmosphere.

8.85 mmol of butyl-octyl-magnesium was introduced into a 150 ml glass reactor. A 20% heptane solution (BOMAG-A) was used giving a feed volume of 10 ml (7.29 g). 17.7 mmol (2.78 ml, 2.32 g) of 2-ethyl-1-hexanol (EHA) was then added at room temperature. The temperature was increased to 60° C. and the reactants were allowed to react with each other at that temperature for 30 min. After this 8.85 mmol (1.28 ml, 1.80 g) of phthaloyl chloride (PDC) was added and the reactants were again allowed to react with each other for 30 min at 60° C. to give the claimed complex.

The resulting solution of the claimed complex was added dropwise into 88.5 mmol (9.73 ml, 16.79 g) of TiCl4 that had been preheated to 95° C. The reactants were also in this case allowed to react with each other for 30 min at 95° C. After this 60 ml of toluene was added. After the precipitate had settled the mother liquid was siphoned off. Five different examples were carried out according to this description. After this the catalyst complex was washed with 30 ml portions of toluene. In Example 8, the complex was washed once with toluene, in Example 9 twice, in Example 10 three times, in Example 11 four times and in Example 12 six times with 30 ml portions of toluene. The toluene washes were carried out at 90° C. Finally, the complex was washed three times with 30 ml portion of pentane. The complexes were finally dried under a stream of nitrogen. The yield of the catalyst was about 2 g which corresponded to about 75% of the theoretical.

Characterization of the Catalyst Components

The catalyst component complexes were analyzed with respect to their Mg, Cl and Ti content. In addition to this, the amount of donor compound, the di-octyl-phthalate (DOP) formed in the synthesis, was measured from the catalysts. To indicate to what degree the formed donor compound (DOP) was decomposing in the synthesis, the amount of phthalic anhydride (PA) was also measured from the catalysts.

IR and X-ray of the Wnwashed Mg:Ti:DOP Complex

A stoichiometric complex of $MgCl_2.TiCl4.DOP$ was prepared by reacting 6.37 mmol (7.19 ml, 5.24 g) of BOMAG with 12.73 mmol (2.00 ml, 1.67 g) of EHA in a 50 ml glass reactor. After this 6.365 mmol (0.92 ml, 1.29 g) of phthaloyl chloride was introduced and last 6.37 mmol (0.70 ml, 1.21 g) of TiCl4 was added. The solid product was washed with pentane and finally, the sample was dried in a stream of nitrogen. The sample was characterized by ER spectroscopy and by means of its X-ray diffraction pattern.

The IR Studies

IR spectres were taken by means of a Nicotet 510 FTIR equipment with 2 $cm^{-1}$ resolution. The number of scans were 128. All the samples were investigated as capillary films between two KBr tablets. The pure EHA was not handled in inert conditions, while the $MgCl_2$ samples were handled in a glovebox in an inert nitrogen environment in order to protect the samples from air and moisture.

X-ray Diffraction Patterns

The WAXS patterns were collected in a reflection ide between 2° and 70° 2Θ with a Siemens D500 instrument. The diffractometer was equipped with a Cu anode and a graphite monochromator in the reflected beam. The CUKα radiation wave-length was 1.541 Å. The effect used was 40 kV and 35 mA. The sample was loaded in a glovebox into a Mylar film covered sample holder.

Bulk Polymerization

The bulk test polymerization was carried out according to the above description relating to the first alternative embodiment.

Results

Preparation of the Complexes

The reaction between the Mg-alkyl and the alcohol resulted in a clear solution with a little bit higher viscosity. The reaction was exothermic as the solution became warm when mixing the reactants, the temperature increase was from room temperature up to 50° C. When the phthaloyl chloride was added a slight yellow colour appeared. Also this reaction was slightly exothermic. The reaction solution become again freely flowing with a low viscosity.

The $TiCl_4$ was introduced into a 150 ml glass reactor and heated to 95° C. The Mg solution was then added to the hot $TiCl_4$ solution dropwise. A beige precipitate started to form right at the beginning of the addition. During addition the solution turned turbid. A partly freely floating precipitate was formed together with more tarlike precipitate that started to foal the reactor walls. To improve the settling conditions toluene was added to the reaction solution. A satisfactory settling of the product was then achieved so that the reaction solution could be siphoned off. Depending on the number of toluene washes the resulting product become more freely flowing. If only one toluene wash was used the product was still as agglomerates, but already two toluene washes resulted in a freely flowing powder-like product.

In the case of the catalyst components of examples 5, 6 and 7, a joined $MgCl_2$-DOP complex and a joined addition to the $TiCl_4$ solution was carried out. After the first toluene wash, ⅓ of the solution slurry was separated. The separated part was then washed with the aliphatic hydrocarbon and dried to give the product of example 5. The remaining part of the slurry was washed a second time with toluene and half of this solution slurry was then taken out from the reactor and undertaken the same hydrocarbon treatment as in Example 5, resulting in the product of Example 6. The remaining part of the catalyst slurry in the reactor was washed twice with toluene and then washed with an aliphatic hydrocarbon in the same way as the first two examples. This sample was the product of example 7. The catalyst morphologies are listed in Table 8.

TABLE 8

The morphology of the catalysts

| Example | Number of toluene washes | Morphology of catalyst |
|---|---|---|
| 8 | 1 | Black agglomerates |
| 9 | 2 | Dark powder |
| 10 | 4 | Dark powder |

The Chemical Composition of the Catalysts

The Mg, Ti, Cl, DOP, EHA and the phthalic anhydride (PA) content of the catalysts were measured. The results are listed in w-% units in Table 9. In Table 10 the chemical composition is given in mol-% units and in Table 11 the Mg and DOP amounts are compared to the Ti amount on a molar basis. Table 12 shows the Cl content of the catalysts.

TABLE 9

The chemical composition of the catalysts in w-% units

| Example | Mg w-% | Ti w-% | DOP w-% | EHA w-% | PA w-% |
|---|---|---|---|---|---|
| 8 | 5.7 | 6.8 | 47.7 | 0.26 | 3.4 |
| 9 | 11.3 | 3.1 | 32.2 | 0.18 | 2.5 |
| 10 | 13.4 | 1.4 | 21.3 | 0.25 | 1.7 |

TABLE 10

The chemical composition of the catalysts in mol-% units

| Example | Mg mol-% | Ti mol-% | DOP mol-% | EHA mol-% | PA mol-% |
|---|---|---|---|---|---|
| 8 | 0.235 | 0.142 | 0.122 | 0.002 | 0.023 |
| 9 | 0.465 | 0.065 | 0.083 | 0.001 | 0.017 |
| 10 | 0.551 | 0.029 | 0.055 | 0.002 | 0.012 |

TABLE 11

The molar proportions between Mg and Ti and between DOP and Ti

| Example | Mg | Ti | DOP |
|---|---|---|---|
| 8 | 1.7 | 1 | 0.86 |
| 9 | 7.2 | 1 | 1.28 |
| 10 | 18.9 | 1 | 1.87 |

TABLE 12

The calculated Cl content in the catalysts compared to the measured amounts

| Example | Calculated Cl w-% | Found Cl w-% |
|---|---|---|
| 8 | 36.8 | 36.4 |
| 9 | 42.2 | 45.0 |
| 10 | 43.3 | 44.5 |

Activity of the Catalysts

All the catalysts were test polymerized according to the above instructions. The polymerization results are listed in Table 13 in both kg PP/g cat and kg PP/g Ti units. Activities of almost 8 kg PP/g cat were achieved. Catalysis of the Examples 8, 9 and 10 gave good polymerization results, with the highest activity achieved for the catalyst that had been twice washed with toluene. The activities expressed in kg PP/g Ti units showed an linear increase related to the number of toluene washes for the catalysts of Examples 8, 9 and 10. Activities of over 500 kg PP/g Ti were reached.

Characterization of the Polymers

All the polymers were characterized with respect to their melt flow rate (OR) and bulk density (BD). All the polymers showed to have a $MFR_2$ between 11–12 g/10 min, indicating a quite good hydrogen response. Bulk densities were between 0.350–0.390 g/ml. The total solubles were between 2 and 3%, being better for the polymers achieved with the catalyst giving higher activity. The results listed in Table 14.

TABLE 13

The polymerization results

| Example | Activity kg PP/g cat | Activity kg PP/g Ti |
|---|---|---|
| 8 | 2.56 | 38 |
| 9 | 7.88 | 254 |
| 10 | 7.33 | 524 |

TABLE 14

The polymer properties

| Example | MFR 2.16 kg, 10 min | TS % | BD g/ml |
|---|---|---|---|
| 8 | 11.0 | 3.1 | 0.360 |
| 9 | 12.37 | 2.1 | 0.350 |
| 10 | 11.0 | 2.1 | 0.390 |

IR Studies of the Catalyst Obtained

IR spectra in the corresponding regions of 1500–1950 $cm^{-1}$ and of 1000–1450 $cm^{-1}$ were taken from the resulting catalyst of example 9 and compared to an IR spectrum of a typical active catalyst complex coming from a synthesis starting from a $MgCl_2.(EtOH)_3$ support material. The spectra are essentially different, and also different from the IR spectra of the isolated complexes of $TiCl_4$/DOP and $MgCl_2$/DOP.

X-ray Studies of the Catalyst Obtained

As described above, X-ray diffraction patterns were taken from the resulting catalysts and compared to a X-ray pattern from an inactive catalyst complex and a typical active catalyst complex prepared from a $MgCl_2.3EtOH$ support material.

In the X-ray patterns of $Mg(OR)_2$, $MgCl_2.TiCl_4.DOP$ produced from $MgCl_2. 3EtOH$, and of $(MgCl_2)$ $1.7.TiCl_4.DOP$ produced by adding one mol $MgCl_2$-DOP to 10 moles of $TiCl_4$, there was a strong peak located between 5° and 9° 2Θ. In addition, there is a halo formation between 17° and 23' 2Θ. The strong peak in the left corner of the pattern indicates that large organic groups are separating metal layers at a distance of between 9 and 17 Å, the distance depending on the size of the organic compound (DOP or di-undecyl phthalate DUP). It can thus be stated that the X-ray diffraction patterns for the final catalyst complexes originating from the claimed complexes all show unique features originating from the starting compounds of $Mg(OR)_2$ and $MgCl_2.DOP$. These patterns show almost no sign of amorphous or crystalline $MgCl_2$.

EXAMPLES 11

Use of the Complex According to the Second Alternative Embodiment and 12 and 13 Use of the Complex According to the Third Alternative Embodiment The following reagents are used; $MgCl_2$ or $MgR_2$, 2-ethyl-hexanol (EHA), phthaloyl dichloride (PDC) and $TiCl_4$ and they are added in the molecular proportion of 1:2:1:1. In the first synthesis (Example 11), the Mg-alkyl is reacted with the alcohol, then the phthaloyl chloride (PDC) is added and finally the $TiCl_4$ is added. In the next two syntheses (Examples 12 and 13), the Mg-alkyl is replaced by $MgCl_2$. Either the $TiCl_4$ or the phthaloyl chloride is added in the next step, followed by the last reagent. The synthesis set-ups are is listed in Table 16.

TABLE 16

Addition order of the reaction components in the catalyst synthesis

| Reaction component/Example | 11 | 12 | 13 |
|---|---|---|---|
| $MgR_2$ | 1 | | |
| $MgCl_2$ | | 1 | 1 |
| R'OH | 2 | 2 | 2 |
| PDC | 3 | 3 | 4 |
| $TiCl_4$ | 4 | 4 | 3 |

Preparation of the Complexes

The same volumes of reagents have been used in all the experiments regardless in which order they have been added. Thus 22.22 mmol (25.10 ml, 18.3 g) of a 20% heptane solution of butyl-octyl-Mg (BOMAG) was added in experiments (8) and (9) and 22.60 mmol (2.15 g) of $MgCl_2$ was added in experiment (10). To this, 45.19 mmol (7.10 ml 5.92 g) of 2-ethyl-1-hexanol EHA was added. The $TiCl_4$ mol amount added was equal to the mol amount of $MgCl_2$ being 22.60 mmol (2.48 ml 4.29 g) and also equal to the mol amount of PDC added, which was 22.60 mmol (3.26 ml, 4.59 g). The addition orders of the reaction components in each catalyst synthesis are listed in Table 16. All the complexes were washed three times with a 100 ml portion of heptane at 90° C. for 15 min and last with a 100 ml portion of pentane at room temperature. Finally the catalysts were dried under a stream of nitrogen.

Characterization of the Catalysts

All the catalysts were characterized with respect to their chemical composition by measuing their Mg, Ti, Cl and di-octyl-phthalate (DOP) content. The Ti and Mg containing catalyst samples were dissolved in a mixture of nitric and hydrofluoric acid and the metals were measured by flame atomic absorption with a nitrous oxide/acetylene flame. Chloride was determined after dissolution in dilute sulphuric acid by potentiometric titration with a standard silver nitrate solution.

The determination of the phthalic esters and the phthalic anhydride were done by first dissolving the sample in acetone. The dissolution was improved by keeping the acetone slurry in an ultra-sound bath for 5 min. After this the samples were filtered and run by solution chromatography. As eluent a solution consisting of water and acetonitrile in a proportion of 4/96 was used. The eluent flow rate was 1.5 ml/min. A photo diode array was used as detector. Each component was identified by comparing its retention time and UV spectra with those of standard components. To further characterize the complexes, IR spectra and X-ray diffraction patterns were taken of them.

Bulk Polymerization

Propylene was polymerized in a stirredtank reactor having a volume of 5 1. About 0.9 ml triethyl aluminium (TEA) as a cocatalyst, about 0 12 ml of a 100-% solution of cyclohexyl methyl dimethoxy silane as an external donor and 30 ml of n-pentane were mixed and allowed to react for 5 minutes. Half of the mixture was added to the polymerization reactor and the other half was mixed with ca 20 mg of said catalyst component. After an additional 5 minutes the catalyst/TEA/donor/n-heptane mixture was introduced into the reactor. The Al/Ti mole ratio was 250 and the Al/external donor mol ratio was 10 mol/mol. 70 mmol of hydrogen and 1400 g of propylene were introduced into the reactor and the temperature was raised within 15–30 minutes to 70° C. The polymerization time was 60 minutes, after which the polymer (0 formed was taken out of the reactor. The polymers were characterized with respect to their Melt Flow Rate (MFR2), bulk density (BD) and the fraction of total solubles in xylene (TS).

Results

Chemical Comnposition of the Catalysts

As stated in the experimental section, the catalysts were characterized with respect to their chemical composition. In Table 17 the chemical composition of the catalysts with respect to the Mg, Ti, di(2-ethyl-1-hexyl)phthalate (DOP), 2-ethyl-1-hexyl alcohol (EHA) and phthalic anhydride PA contents are listed in w-% units and in Table 18 the same species are listed in mol-% units and last, in Table 19 the molar composition between Mg, Ti and DOP are listed. The Examples 11 and 13 are represented by two catalysts, 11a and 11b, as well as 13a and 13b, respectively. The chlorine contents are listed in Table 20.

TABLE 17

The Mg, Ti, DOP, EHA and PA contents of the catalysts in w-% units

| Example | Mg w-% | Ti w-% | DOP w-% | EHA w-% | PA w-% |
|---|---|---|---|---|---|
| 11a | 3.6 | 5.6 | 35.6 | 6.8 | 4.16 |
| 11b | 9.9 | 3.5 | 34.0 | — | — |
| 12 | 3.9 | 7.0 | 35.7 | 5.3 | 1.27 |
| 13a | 4.5 | 7.0 | 43.6 | 5.15 | 1.6 |
| 13b | 11.1 | 3.7 | 33.0 | 1.00 | 0.3 |

TABLE 18

The Mg, Ti, DOP, EHA and PA contents of the catalysts in mol-% units

| Example | Mg mol-% | Ti mol-% | DOP mol-% | EHA mol-% | PA mol-% |
|---|---|---|---|---|---|
| 11a | 0.148 | 0.117 | 0.091 | 0.052 | 0.028 |
| 11b | 0.407 | 0.073 | 0.087 | — | — |
| 12 | 0.161 | 0.146 | 0.091 | 0.041 | 0.009 |
| 13a | 0.185 | 0.146 | 0.112 | 0.040 | 0.011 |
| 13b | 0.457 | 0.077 | 0.085 | 0.008 | 0.002 |

TABLE 19

Comparison between the molar amounts of Mg, Ti and DOP

| Example | Mg/Ti | Ti | DOP/Ti |
|---|---|---|---|
| 11a | 1.3 | 1 | 0.8 |
| 11b | 5.6 | 1 | 1.2 |
| 12 | 1.1 | 1 | 0.6 |
| 13a | 1.3 | 1 | 0.8 |
| 13b | 5.6 | 1 | 1.1 |

TABLE 20

The calculated amounts of Cl in the catalysts compared to the amounts found

| Example | Calculated w-% | Found w-% |
|---|---|---|
| 11a | 27.1 | 26.0 |
| 11b | 39 | — |
| 12 | 32.1 | 30.9 |
| 13a | 33.5 | 32.4 |
| 13b | 43.4 | 44.0 |

The IR Results

In the IR spectra of the catalyst components of Examples 12 and 13a. There were clear indications of the presence of phthalic anhydride in the catalyst that has been prepared from MgR$_2$ (Example 11a). The phtalic anhydride was almost totally missing from the samples that had been prepared out of MgCl$_2$ (Examples 12 and 13a). These results confirm the results of the chemical analysis. The IR spectrum (not shown) for the toluene washed example 10b catalyst showed no traces of phthalic anhydride but to the left of the C=O—Ti peak a shoulder had appeared indicating the presens of some free carboxylic acid group (—COOH).

The X-Ray Diffraction Patterns

The X-ray diffraction patterns for the catalysts show that the addition of TiCl$_4$ before PDC gives a more crystalline material. Example 12 is still showing the organic separation peak at 7° 2Θ and the halo between 18° and 22° 2Θ but only a slight remain thereof can be seen of the halo in the spectrum of Example 13a. In all patterns there seems to be an additional peak at about 32°–33° 2Θ. This peak is not connected to crystalline MgCl$_2$. Some unreacted MgCl$_2$ seems to be present in the catalyst component of Example 13a which is starting to dominate when the catalyst is washed with toluene.

Polymerization Results

All but one (Example 11a) of the catalysts were test polymerized according to the descriptions in the experimental section. The polymerization results both in kg PP/g cat units and in kg PP/g Ti units are listed in Table 21. There was an almost logaritmic linear increase in the activities. As a whole it can be said that:

1. Addition of TiCl$_4$ before PDC gives better activity (compare Examples 12 and 13).
2. Starting from MgCl$_2$ instead of from MgR$_2$ gives higher activity (compare Example 11 with Examples 12 and 13).
3. Toluene wash improves activity (compare Examples 13a and 13b).

TABLE 21

The polymerization results

| Example | Activity kg PP/2 cat. | Activity kg PP/g Ti |
|---|---|---|
| 11b | 0.06 | 1.3 |
| 12 | 0.4 | 6.0 |
| 13a | 1.2 | 18 |
| 13b | 2.5 | 67 |

SUMMARY

In this study a stoichiometric synthesis route was used to produce the MgCl$_2$—C$_6$H$_4$L(COOR')$_2$ complex. MgCl$_2$ and Mg-alkyl have been reacted with an alcohol to form a MgCl$_2$-Mg-alcoholate complex, a Mg-alcoholate and an MgCl$_2$-alcohol complex. These Mg-alcoholates or MgCl$_2$-alcohol complex has then been brought into contact with phthaloyl chloride to give an MgCl$_2$-donor complex. It was not possible to produce an MgCl$_2$-donor complex of this type through a direct contact between MgCl$_2$ and the corresponding donor, which rules out the possibility that this complex could have been formed unintactionally in the prior art. The complex achieved trough the synthesis routes described in this study is identifiable through its distinct X-ray diffraction pattern that shows a dominant peak at 4.5° 2Θ. IR studies showed that the Mg in the MgCl$_2$ is co-ordinated both to the C=O oxygen and the C—O— oxygen in the ester group.

What is claimed is:

1. A soluble complex comprising a magnesium dihalide and an electron donor represented by the following formula (I) expressing the molar ratio between the magnesium dihalide and the electron donor:

$$MgX_2 \cdot [(R(OR')_n]_m \quad (I)$$

wherein $MgX_2$ is the magnesium dihalide and $R(OR')N$ is the electron donor, X is a halogen, R is an n-valent $C_1$–$C_{20}$ aliphatic group, an n-valent $C_7$–$C_{27}$ araliphatic group or an n-valent $C_2$–$C_{22}$ acylic group, R' is a $C_1$–$C_{20}$ alkyl group or a $C_7$–$C_{27}$ aralkyl group, n is a number from 1 to 6 and m is defined as a number $0.5 \leq m \leq 2.0$.

2. The complex according to claim 1, wherein X is selected from the group consisting of Cl, Br and I.

3. The complex according to claim 1, wherein R is an n-valent $C_2$–$C_{22}$ acylic group.

4. The complex according to claim 1, wherein R' is a $C_6$–$C_{16}$ alkyl group.

5. The complex according to claim 1, wherein n is 1 to 4.

6. The complex according to claim 1, wherein m is 0.67 to 1.0.

7. The complex according to claim 1, wherein Formula I is replaced with a magnesium dichloride phthalic acid ester complex having the formula (II):

$$MgCl_2 \cdot C_6H_4(COORC')_2 \qquad (II)$$

wherein R' is the same as in claim 1.

8. The complex according to claim 1, wherein formula I is replaced with a magnesium dichloride phthalic acid ester complex having the formula (III):

$$(MgCl_2)_3 \cdot [C_6H_4(COOR')_2]_2 \qquad (III)$$

wherein R' is the same as in claim 1.

9. The complex according to claim 1, wherein the complex has an X-ray diffraction pattern having a dominant peak at 4.5°2θ.

10. A process for the preparation of a soluble complex according to claim 1, comprising reacting a magnesium compound (a) containing an alkoxy moiety, which magnesium compound is selected from the group consisting of a complex of a magnesium dihalide and a magnesium dialkoxide, a complex of a magnesium dihalide and an alcohol, and a non-complex magnesium dialkoxide, with a halogen compound (b), which is capable of forming the electron donor by replacement of its halogen by said alkoxy moiety, to yield a solution of said soluble complex.

11. The process according to claim 10, wherein said halogen compound (b) is represented by the formula (IV):

$$RXn \qquad (IV)$$

wherein R is an n-valent $C_1$–$C_{20}$ aliphatic group, an n-valent $C_7$–$C_2$araliphatic group or an n-valent $C_2$–$C_{22}$ acylic group, X is a halogen and n is 1 to 6.

12. The process according to claim 11, wherein R is an n-valent $C_2$–$C_{22}$ acylic group.

13. The process according to claim 11, wherein X is selected from the group consisting of Cl, Br and I.

14. The process according to claim 11, wherein n is 1 to 4.

15. The process according to claim 11, wherein said halogen compound is an organic acid halide.

16. The process according to claim 10, wherein said complex of a magnesium dihalide and said magnesium dialkoxide are each a magnesium dichloride-magnesium dialkoxide complex of the formula (V):

$$MgCl_2 \cdot [Mg(OR')_2]_p \qquad (V)$$

wherein R' is a $C_1$–$C_{20}$ alkyl group or a $C_1$–$C_{27}$ aralkyl group, and p is 1 to 6.

17. The process according to claim 16, wherein formula (V) is replaced with formula (VI):

$$MgCl_2 \cdot [Mg(OR')_2]_p \qquad (VI)$$

wherein R' is a $C_1$–$C_{20}$ alkyl group or a $C_7$–$C_{27}$ aralkyl group.

18. The process according to claim 16, wherein said magnesium dichloride magnesium dialkoxide complex is prepared by reacting magnesium dichloride with an alcohol into an intermediate which is a magnesium dichloride alcohol complex $MgCl_2 \cdot (R'OH)_{2p}$, wherein R' is the same as in claim 16, and reacting the magnesium dichloride alcohol complex with p mol of a magnesium dialkyl $MgR''_2$, wherein R'' is a hydrocarbyl group having 1 to 20 carbon atoms.

19. The process according to claim 18, wherein independently, the molar ratio $MgCl_2$:R'OH is between 1:1 and 1:8, the molar ratio $MgCl_2 \cdot (R'OH)_{2p}$:$MgR_{12}$ is between 1:1 and 1:4, the temperature is between 80° C. and 160° C., and the reaction time is about 2 h to about 8 h.

20. The process according to claim 15, wherein said magnesium compound (a) is reacted with said halogen compound (b), wherein compound (b) is phthalic acid dichloride $Ph(COCl)_2$, wherein Ph is o-phenylene, and compound (a) is magnesium dichloride-dimagnesium dialkoxide complex $MgCl_2 \cdot [Mg(OR')_2]_2$, wherein R' is a $C_6$–$C_{16}$ alkyl group.

21. The process according to claim 10, wherein said non-complex magnesium dialkoxide has the formula (VII):

$$Mg(OR')_2 \qquad (VII)$$

wherein R' is a $C_1$–$C_{20}$ alkyl group or a $C_7$–$C_{27}$ aralkyl group.

22. The process according to claim 21, wherein said non-complex magnesium dialkoxide is prepared by reacting a magnesium dialkyl represented by the formula $MgR''_2$, wherein R'' is a hydrocarbyl group having 1 to 20 carbon atoms, with an alcohol represented by the formula R'OH wherein R' is the same as in claim 21.

23. The process according to claim 15, wherein said magnesium compound (a) which is a non-complex magnesium dialkoxide represented by the formula $Mg(OR')_2$, wherein R' is a $C_1$–$C_{20}$ alkyl or a $C_7$–$C_{27}$ aralkyl is reacted with said halogen compound (b) which is a phthalic acid dichloride $Ph(COCl)_2$, wherein Ph is o-phenylene.

24. The process according to claim 10, wherein said complex of a magnesium dihalide and a magnesium dialkoxide is a complex of a magnesium dichloride and an alcohol having the formula (VIII):

$$MgCl_2 \cdot (R'OH)_q \qquad (VIII)$$

wherein R' is a $C_1$–$C_{20}$ alkyl or a $C_7$–$C_{27}$ aralkyl group, and q is from 1 to 6.

25. The process according to claim 24, wherein said complex of a magnesium dihalide and an alcohol is prepared by reacting magnesium dichloride $MgCl_2$ and an alcohol R'OH, wherein R' is the same as in claim 24.

26. The process according to claim 24, wherein the reaction temperature is kept between 10° C. and 100° C., and the reaction time is about from 10 to about 90 min.

27. The process according to claim 15, wherein said magnesium compound (a), which is said complex of a magnesium dihalide and an alcohol having the formula $MgCl_2 \cdot (R'OH)_q$, wherein R' is a $C_1$–$C_{20}$ alkyl or a $C_7$–$C_{27}$ aralkyl and q is from 1 to 6, is reacted with said halogen compound (b) which is said phthalic acid dichloride $Ph(COCl)_2$, wherein Ph is o-phenylene.

28. The process according to claim 10, wherein said magnesium compound (a) and said halogen compound (b) are reacted stoichiometrically.

* * * * *